United States Patent [19]

Sand et al.

[11] Patent Number: 5,536,646
[45] Date of Patent: Jul. 16, 1996

[54] SIMPLIFIED EXTRACTION METHOD FOR BACTERIAL ANTIGENS USING DRIED REAGENTS

[75] Inventors: Theodore T. Sand, Poway; James A. Gordon; Allan D. Pronovost, both of San Diego, all of Calif.

[73] Assignee: Quidel Corporation, San Diego, Calif.

[21] Appl. No.: 203,878

[22] Filed: Feb. 24, 1994

Related U.S. Application Data

[63] Continuation of Ser. No. 831,273, Feb. 4, 1992, abandoned.

[51] Int. Cl.[6] .......................... C12Q 1/14; A61K 31/185; A61K 33/00
[52] U.S. Cl. .................. 435/36; 435/34; 435/7.34; 514/553; 424/718; 536/124; 536/127
[58] Field of Search .................... 435/34, 36, 7.34; 514/553; 424/718; 536/124, 127

[56] References Cited

U.S. PATENT DOCUMENTS

| | | | |
|---|---|---|---|
| Re. 33,850 | 3/1992 | Snyder et al. | 435/36 |
| 4,673,639 | 6/1987 | Slifkin | 435/36 |
| 4,808,524 | 2/1989 | Snyder et al. | 435/36 |
| 4,847,199 | 7/1989 | Snyder et al. | 435/36 |
| 5,415,994 | 5/1995 | Imrich et al. | 435/5 |

FOREIGN PATENT DOCUMENTS

WO/87/01393  3/1987  WIPO.

OTHER PUBLICATIONS

Slifkin et al; J. Clin. Microbiol. 20(1):12–14 (Jul. 1984).
Miller et al; J. Clin. Microbiol. 20(5):846–848 (Nov. 1984).
Schwabe et al; J. Clin. Microbiol. 25(2):309–311 (Feb. 1987).
Facklam; J. Clin. Microbiol. 25(3):504–508 (Mar. 1987).
Mackenzie et al; Can. Med. Assoc. T. 138:917–919 (May 1988).
Lennette, E. H., Ed., *Manual of Clinical Microbiology*, Fourth Edition, American Society of Microbiology, Washington, D.C., (1985) pp. 170–171.

*Primary Examiner*—John W. Rollins
*Assistant Examiner*—Francisco C. Prats
*Attorney, Agent, or Firm*—Morrison & Foerster

[57] ABSTRACT

Polysaccharide antigens characteristic of Group A or B Streptococci are extracted for use in immunodiagnostic assays by a simplified method. The method involves the use of two dried reagents, sodium nitrite and Tris base, and a liquid reagent, acetic acid.

10 Claims, No Drawings

SIMPLIFIED EXTRACTION METHOD FOR BACTERIAL ANTIGENS USING DRIED REAGENTS

This application is a continuation of application Ser. No. 07/831,273, filed Feb. 4, 1992.

TECHNICAL FIELD

The present invention relates to a process for the extraction of polysaccharide antigens from organisms. More specifically, it relates to the extraction of saccharide antigens characteristic of organisms in the family Streptococcaceae, including Group A and Group B Streptococci.

BACKGROUND OF THE INVENTION

The traditional method for extraction of saccharide antigens characteristic of Group A Streptococci (GAS) involves the use of all liquid reagents. See e.g. *Manual of Clinical Microbiology*, 4th ed. (1985), page 171. This method is well known and can be used for diagnosis of streptococcal infection when performed in conjunction with an immunoassay. Typically, the extraction involves three liquid reagents: an acid (usually acetic acid, hydrochloric acid or citric acid), sodium nitrite and a neutralizing base or buffer (Tris, sodium hydroxide, etc.). These reagents are matched in terms of pH and molarity to produce optimal release of GAS saccharide antigen. A typical extraction involves the use of 150 μl of 2M sodium nitrite, 150 μl of 2M acetic acid and 350 μl of 0.44M Tris/0.66N sodium hydroxide. The first two reagents (sodium nitrite and acetic acid) are mixed together in a tube and a swab containing the sample is placed into the solution. The reaction is incubated for 1 to 3 minutes and the third (neutralizing) solution is added and mixed. The swab is removed, a tip is inserted into the tube and the contents of the tube squeezed out onto a test device.

The procedure described above requires that accurate volumes of the three reagents be dispensed since the pH of the final solution must be approximately 7–8 in order to allow for the capture and detection of the released antigens in an immunodiagnostic assay.

DISCLOSURE OF THE INVENTION

The present invention simplifies the extraction process described previously and thereby reduces the potential for variability among test results. The result of this simplification is the development of an extraction process with two dried components and a single liquid reagent.

One embodiment of the invention is a method of extracting polysaccharide analytes from a clinical sample. The clinical sample is incubated with a first absorbent material impregnated with a nitrite salt, an acid solution is added and is followed by the addition of a second absorbent material impregnated with a neutralizing base or buffer.

A second aspect of the invention is a method of extracting polysaccharide antigens from a clinical sample. Sodium nitrite is absorbed onto a first absorbent material and a neutralizing buffer is absorbed onto a second absorbent material. These materials are dried and later incubated with the clinical sample and an acid solution. The resultant solution is deposited onto a test device that will indicate the presence of the polysaccharide antigen.

Yet another aspect of the invention is a method of extracting polysaccharide antigens characteristic of Group A streptococci from a clinical sample. Sodium nitrite is absorbed onto a 7 mm diameter disk of S&S #903 paper, and Tris is absorbed into a dispense tube tip containing a cotton plug and a 6 mm diameter disk of S&S #300 paper. These materials are dried and the clinical sample is incubated with the dried sodium nitrite and an acetic acid solution. The resultant solution is squeezed through the dispense tube tip containing the Tris and deposited onto a test device that will indicate the presence of the polysaccharide antigen characteristic of Group A streptococci.

A second embodiment of the invention is directed to a kit for use in the process to extract polysaccharide analytes from a clinical sample. The kit comprises a package containing a first absorbent material impregnated with a premeasured amount of a nitrite salt, a second absorbent material impregnated with a premeasured amount of a neutralizing buffer, and a premeasured amount of an acid.

DETAILED DESCRIPTION OF THE INVENTION

The method of the invention is useful for the extraction of polysaccharide analytes from clinical samples. More particularly, the method is useful for the extraction of polysaccharide antigens from clinical samples wherein the existence of the antigens indicates the presence of a particular organism in the clinical sample. Earlier methods required accurate measurement of three reagents for the extraction. The simplified extraction method of the present invention uses two dried reagents and a single liquid reagent.

The invention is useful for the extraction of polysaccharide antigens characteristic of particular organisms. The invention has been demonstrated to be useful for the extraction of polysaccharide antigens characteristic of organisms in the family Streptococcaceae, and especially polysaccharide antigens characteristic of Group A and Group B Streptococci. Accordingly, while the invention is described and exemplified below with respect to the extraction of polysaccharide antigens characteristic of Group A Streptococci, it will be appreciated that these teachings may be extended to polysaccharide analytes characteristic of other types of conditions such as Group B or C Streptococci and Candida species.

A. Clinical Samples

Clinical samples that are tested using the method of the invention will typically be swab specimens collected from patients who are thought to be suffering from streptococcal infections. Where the organism is Group A streptococci, a pharyngeal swab specimen will be collected, but where Group B streptococci is suspected, a vaginal swab specimen will be collected.

After collection, the swab may be stored for up to 24 hours prior to extraction. Following extraction according to the invention, the extractant must be analyzed for the presence of the streptococci-characteristic antigen within an hour.

B. The Materials

In the original process for the extraction of streptococcal colonies, 150 μl of 2M sodium nitrite solution was mixed with 150 μl of 2M acetic acid to form a solution into which is placed the clinical specimen. A neutralizing buffer containing 350 μl of a solution of 0.44M Tris and 0.66N sodium hydroxide was added to the sodium nitrite/acid solution such that the pH of the final solution was in the range of 7–8 to allow for the capture and detection of the polysaccharide antigen characteristic of streptococcus in an immunodiagnostic assay.

The present invention involves the use of a nitrite salt solution that has been absorbed onto filter materials and dried. In the preferred embodiment, the solution is a sodium nitrite solution wherein the concentration of sodium nitrite can be in the range of 1 to 8M at a volume in the range of 300 to 37.5 μl, but is most preferably 50 μl at 6M.

The sodium nitrite solution is absorbed onto filter materials such as cotton, glass fiber, filter paper, and combinations thereof. The preferable material was found to be a S&S #903 paper disk approximately 7 mm in diameter. The sodium nitrite containing disk is allowed to dry overnight (at least 18 hours) at 15° to 100° C., preferably 45° C.

The neutralizing base or buffer of the present invention is constructed from standard base or buffer systems appropriate to obtain and/or maintain the desired pH, such as Tris, sodium hydroxide, sodium bicarbonate, amino methyl propanol, 3-[cyclohexylamino]-1-propane-sulfonic acid (CAPS) and N-tris-[hydroxymethyl]methyl-3-aminopropane sulfonic acid (TAPS). The preferred neutralizing buffer of the present invention is Tris base at a concentration of between 0.5 and 4M at a volume of between 700 and 87.5 μl, but most preferably 100 μl at 3.5M.

The neutralizing base or buffer is absorbed onto filter materials such as glass fiber, cotton, filter paper and combinations thereof. The preferable configuration was found to be a dispense tube tip with a cotton plug and a S&S #300 paper disk approximately 6 mm in diameter. The buffer containing materials are then dried at 15° to 100° C., preferably 45° C.

The acid of the present invention may include acetic acid, citric acid, oxalic acid or hydrochloric acid, among others. The preferred acid of the present invention is acetic acid at a concentration of between 0.05 and 2M at a volume in the range of between 0.1 and 5 mls, but most preferably 0.6 mls at 0.5M.

C. The Extraction Process

Filter materials containing sodium nitrite and Tris are prepared as described above. The disk containing the sodium nitrite is placed into the dispense tube. The acetic acid solution is added and the swab containing the specimen is then inserted into the dispense tube and allowed to incubate for up to 30 minutes. The dispense tube tip containing the Tris impregnated cotton plug and S&S #300 paper disk is inserted into the dispense tube. The dispense tube is inverted and the solution is squeezed out onto a test device such as QTEST Strep™ (Becton Dickenson) and ALERT Strep™ (Quidel) that will indicate the presence or absence of the streptococcus- characteristic antigen.

The invention is further illustrated by the following examples. These examples are not intended to limit the invention in any manner.

EXAMPLES

Example I

Optimization of the Extraction Process

The method developed to replace the current 3-liquid reagent protocol involved optimizing the volume and concentration of sodium nitrite, Tris and acetic acid. The sodium nitrite and Tris were optimized to be absorbed onto filter paper materials and dried down. The acetic acid reagent was altered in concentration since it was the only liquid reagent remaining in the extraction.

The original neutralizing reagent (Tris/NaOH in the original method) was modified to include a higher concentration of Tris and no NaOH. Approximately 100 to 150 μl of Tris base at 3.5M gave sufficient neutralization. Sodium bicarbonate, amino methyl propanol, CAPS and TAPS also were evaluated. However, the Tris buffer was found to perform the best when absorbed onto a variety of materials and dried overnight at 45° C. Materials evaluated for containing the neutralizing reagent included: glass fiber, cotton, S&S #300 paper and combinations thereof. The best performance was obtained with a dispense tube tip containing S&S #300 paper disk approximately 6 mm in diameter and a cotton plug. This arrangement was found to hold 100 μl of 3.5M Tris base, to dry down readily and to neutralize the pH of the test solution when used in a functional test.

Sodium nitrite was modified by increasing the molarity of the solution. A volume of 50 μl was found to be completely contained by the S&S #903 paper disk that would be placed in the dispense tube. Several materials (cotton, glass fiber) were evaluated, but a disk, approximately 7 mm in diameter of S&S #903 was found to give the best performance. Since 50 μl was the target volume, this required that a 6M sodium nitrite solution be used.

The acetic acid reagent was optimized by increasing the volume used per extraction from 150 to 600 μl and by decreasing the molarity of acetic acid from 2M to 0.5M.

Example II

Specimen Extraction and Testing

50 μl of 6M sodium nitrite was absorbed onto a 7 mm diameter disk of S&S #903 paper and allowed to dry for at least 18 hours at 45° C. 100 μl of 3.5M Tris base was absorbed onto a cotton plug and a 6 mm disk of S&S #300 paper that were placed into a dispense tube tip. The assembly was allowed to dry for at least 18 hours at 45° C. The sodium nitrite containing disk and a solution of 600 μl of 0.5M acetic acid were placed into the dispense tube. This procedure was carried out twice such that two dispense tubes contained acetic acid and filter paper containing dried sodium nitrite. A solution containing Group A streptococci was placed into one of the dispense tubes. A dispense tube tip containing the dried Tris base was inserted into each dispense tube and the solutions from the dispense tubes were squeezed through the tip and onto a QTEST Strep™ (Becton Dickenson). Table I lists the test results.

Control samples were run using the previously described method for extraction wherein 150 μl of 2M sodium nitrite and 150 μl of 2M acetic acid are mixed together in a dispense tube. This process was carried out twice such that two dispense tubes contained sodium nitrite and acetic acid. A solution containing Group A streptococci was placed into one of the dispense tubes. The reaction was incubated for 1 minute. 350 μl of 0.44M Tris/0.66N sodium hydroxide solution was then added to each dispense tube and the solutions in each tube were mixed. A dispense tube tip was then inserted into the dispense tube and the contents of the dispense tube were squeezed onto a QTEST Strep™ (Becton Dickenson). The results are compiled in Table I.

TABLE I

|  | Visual Result | |
| --- | --- | --- |
|  | Negative | Positive |
| Control Extraction Process (all liquid reagents) | − | + |
| Dried Components Extraction Process | − | + |

Modifications of the above described mode for carrying out the invention that are obvious to those of skill in the fields of biochemistry, organic chemistry, medical diagnostics and related fields are intended to be within the scope of the following claims.

We claim:

1. A method for simultaneously neutralizing and applying an extract of polysaccharide antigens characteristic of Group A or Group B streptococci to a test device which method comprises:

filtering said extract through a filter material onto the test device wherein said filter material contains neutralizing base or buffer in an amount effective to obtain or maintain the desired pH absorbed and dried thereon;

wherein said extract has been prepared by extracting a clinical sample suspected of containing said Group A or Group B streptococci with nitrous acid.

2. The method of claim 1 wherein said extracting is conducted by contacting said sample with the combination of (a) a filter material to which a nitrite salt solution has been absorbed and dried; and (b) an aqueous solution of an acid.

3. The method of claim 2 wherein the acid is selected from the group consisting of acetic acid, citric acid, oxalic acid and hydrochloric acid.

4. The method of claim 1 wherein the polysaccharide antigen is characteristic of Group A Streptococci and the clinical sample is a pharyngeal secretion.

5. The method of claim 1 wherein the polysaccharide antigen is characteristic of Group B Streptococci and the clinical sample is a vaginal secretion.

6. The method of claim 1 wherein the neutralizing base or buffer is selected from the group consisting of Tris, sodium hydroxide, sodium bicarbonate, amino methyl propanol, 3-[cyclohexylamino]-1-propane sulfonic acid (CAPS) and N-tris-[hydroxymethyl]methyl-3-aminopropane sulfonic acid (TAPS).

7. The method of claim 6 wherein the neutralizing base is Tris base.

8. The method of claim 3 wherein the acid is acetic acid.

9. The method of claim 2 wherein the filter material is at least one material selected from the group consisting of cotton, glass fiber and filter paper.

10. The method of claim 9 wherein the filter material is filter paper.

* * * * *